United States Patent [19]
Wilson et al.

[11] Patent Number: 5,611,793
[45] Date of Patent: Mar. 18, 1997

[54] LASER TREATMENT

[75] Inventors: Michael Wilson, London, Great Britain; Wilson Harvey, Gargunnock, United Kingdom

[73] Assignee: Institute of Dental Surgery, London, Great Britain

[21] Appl. No.: 325,322

[22] PCT Filed: Apr. 30, 1993

[86] PCT No.: PCT/GB93/00909

§ 371 Date: Oct. 25, 1994

§ 102(e) Date: Oct. 25, 1994

[87] PCT Pub. No.: WO93/21992

PCT Pub. Date: Nov. 11, 1993

[30]     Foreign Application Priority Data

Apr. 30, 1992 [GB] United Kingdom .................. 9209379
May 26, 1992 [GB] United Kingdom .................. 9211138

[51] Int. Cl.$^6$ .................................................. A61B 17/32
[52] U.S. Cl. ............................ 606/2; 433/216; 433/229
[58] Field of Search ............................. 606/3, 10, 15, 606/16; 607/88, 89; 433/215, 226, 216, 229; 128/898

[56]            References Cited

U.S. PATENT DOCUMENTS

| | | |
|---|---|---|
| 3,769,963 | 11/1973 | Goldman et al. . |
| 3,900,034 | 8/1975 | Katz et al. . |
| 4,336,809 | 6/1982 | Clark . |
| 5,007,837 | 4/1991 | Werly ...................................... 433/226 |
| 5,020,995 | 6/1991 | Levy . |
| 5,092,773 | 3/1992 | Levy . |
| 5,118,293 | 6/1992 | Levy . |
| 5,123,902 | 6/1992 | Müller et al. . |
| 5,151,029 | 9/1992 | Levy . |
| 5,151,031 | 9/1992 | Levy . |
| 5,188,532 | 2/1993 | Levy . |

FOREIGN PATENT DOCUMENTS 2125986   3/1984   United Kingdom .
2202442   9/1988   United Kingdom .

OTHER PUBLICATIONS

Dobson, J. et al. (1992) "Sensitization of oral bacteria in biofilms to killing by light from a low–power laser", *Archs oral Biol.* 37(No. 11):883–887.

Friedberg, J.S. et al., (1991) "Antibody–Targeted Photolysis Bacteriocidal Effects of Sn (IV) Chlorin $e_6$–Dextran–Monoclonal Antibody Conjugates" *Ann. N.Y. Acad. of Sci.* 618:383–393.

Pearce, E.L.F. et al., (1988) "In vivo Comparison of Caries Inhibition by a Plaque Mineral Enriching Mouthrinse and a Fluoride Dentifrice" *Caries Research* 22:362–370.

Macmillan, J.D. et al., (1966) "Lethal Photosensitization of Microorganisms with Light from a Continuous–wave Gas Laser" *Photochem. Photobiol.* 5:555–565.

Malik, Z. et al., (1990) "Bactericidal Effects of Photoactivated Porphyrins—An alternative Approach to Antimicrobial Drugs" *J. of Photochem. Photobiol, B: Biol.* 5:281–293.

Okamata, H. et al., (1992) "Dye–Mediated Bactericidal Effect of He–Ne Laser Irradiation on Oral Microorganisms" *Laser Surg. Med.* 12:450–458.

Wilson, M. et al., (1993) "Sensitization of periodontopathogenic bacteria to killing by light from a low–power laser" *Oral Microbiol. Immunol.* 8:182–187.

Wilson, M. (1993) "Sensitization of *Streptococcus sanguis* to Killing by Light from a Helium/Neon Laser" *Lasers Med. Sci.* 8:69–73.

Meyer, M., (1991) "A study of the effects of photodynamic therapy on the normal tissues of the rabbit jaw" *Br. J. Cancer* 64:1093–1097.

*Primary Examiner*—Angela D. Sykes
*Assistant Examiner*—Sonya Harris-Ogugua
*Attorney, Agent, or Firm*—Reed & Robins

[57]            ABSTRACT

A method of disinfecting or sterilizing tissues of the oral cavity or a wound or lesion in the oral cavity is provided. The method comprises applying a photosensitizing compound to said tissues, wound or lesion and irradiating said tissues, wound or lesion with laser light at a wavelength absorbed by said photosensitizing compound.

18 Claims, No Drawings

LASER TREATMENT

The present invention relates to the use of photosensitising compounds and laser irradiation to kill the microbes involved in a number of oral diseases including inflammatory periodontal disease and caries or in wound infections and in disinfecting or sterilising wounds and other lesions in the oral cavity.

Inflammatory periodontal diseases are the most prevalent diseases of humans and the advanced form, chronic periodontitis, is the major cause of tooth loss in adults. Current methods of treating chronic periodontitis involve removal of subgingival plaque in order to eliminate the causative organisms; this is often supplemented by antimicrobial chemotherapy. Mechanical removal of plaque is never fully successful and there are many disadvantages in the long-term use of antimicrobial agents such as chlorhexidine and tetracycline, notably the development of resistance rendering the agents clinically ineffective and difficulties arising from disturbance of the oral microflora.

There is also a need to destroy microorganisms in drilled-out carious cavities prior to conventional filling and during other forms of dental surgery.

Another situation requiring destruction of microbes in the oral cavity is in the case of oral candidiasis of AIDS patients, immunocompromised individuals and patients with denture stomatitis where conventional treatment by chemotherapy is only poorly effective.

The present inventors have developed a method for destroying disease-related microbes in the oral cavity.

Accordingly, the present invention provides a method for disinfecting or sterilising tissues in the oral cavity or a wound or lesion in the oral cavity, which method comprises applying a photosensitising compound to the tissues, wound or lesion and irradiating the tissues wound or lesion with laser light at a wavelength absorbed by the photosensitising compound.

The invention also provides the use of a photosensitising compound in the manufacture of a medicament for use in disinfecting or sterilising tissues of the oral cavity or a wound or lesion in the oral cavity by (a) contacting the tissues, wound or lesion with the photosensitising compound such that any disease-related microbes in the tissues, wound or lesion take up the photosensitising compound and (b) irradiating the tissues, wound or lesion with laser light at a wavelength absorbed by the photosensitising compound.

The wound or lesion treated may be any surgical or trauma-induced wound, a lesion caused by a disease-related microbe, or a wound or lesion infected with such a microbe. The treatment may be applied to disinfect or sterilise a wound or lesion as a routine precaution against infection or as a specific treatment of an already diagnosed infection of a wound or lesion.

In one aspect the present invention provides a method for destroying disease-related microbes in the oral cavity which method comprises applying a photosensitising compound to the microbes and irradiating the microbes with laser light at a wavelength absorbed by the photosensitising compound.

The invention further provides the use of a photosensitising compound in the manufacture of a medicament for use in destroying disease-related microbes in the oral cavity by (a) contacting the microbes with the photosensitising compound such that the microbes take up the photosensitising compound and (b) irradiating the microbes with laser light at a wavelength absorbed by the photosensitising compound.

In preferred aspects of the invention the treatment with photosensitising compound and laser irradiation are applied to (i) destruction of disease-related microbes in a periodontal pocket in order to treat chronic periodontitis;

(ii) destruction of disease-related microbes in the region between the tooth and gingiva (gingival crevice or gingival margin) in order to treat or prevent inflammatory periodontal diseases including chronic periodontitis, gingivitis and the like;

(iii) disinfection or sterilisation of drilled-out carious lesions prior to filling;

(iv) destruction of cariogenic microbes on a tooth surface in order to treat or prevent dental caries.

(v) disinfection or sterilisation of dental and/or gingival, tissues in other dental surgical procedures and (vi) treatment of oral candidiasis, in AIDS patients immunocompromised patients or those with denture stomatitis.

Photosensitising compounds for use in accordance with the present invention are generally non-toxic to the target microbes at concentrations envisaged in accordance with the invention and to the tissues surrounding the wound or lesion. However there is no particular requirement that the photosensitisers should be non-toxic to the microbes. Moreover, since exposure of the surrounding tissues of the oral cavity to the photosensitiser will generally be of short duration and highly localised, it may be acceptable to use compounds which have some slight toxicity to these tissues.

It is preferred that the photosensitisers used in the method of the invention will be capable of absorbing laser light at the red end of the visible spectrum or at longer wavelengths since such laser light will be better able to penetrate tissues surrounding a wound or lesion, such as oral tissues, and, in particular, blood which may be present in the sites to be treated. It is generally preferred that the photosensitiser selected for use has a positive charge under physiological conditions since such photosensitisers are more readily taken up by the target microbes, however the phthalocyanines, which in accordance with the invention are effective against bacteria, are negatively charged. Particular photosensitisers which may be used in accordance with the invention include dyes and other photosensitising compounds such as:

arianor steel blue toluidine blue O tryptan blue crystal violet methylene blue azure blue cert azure B chloride azure 2 azure A chloride azure B tetrafluoroborate thionin azure A eosinate azure B eosinate azure mix sicc.

azure II eosinate haematoporphyrin HCl haematoporphyrin ester aluminium disulphonated phthalocyanine chlorins.

Some of these photosensitisers are not well taken up by Gram negative organisms in particular the haematoporphyrins, and it is preferred to use those which are effective against Gram negative organisms, i.e. the dyes. Of these it is currently preferred to use aluminium disulphated phthalocyamine, toluidine blue O, azure B chloride or methylene blue.

Preferably the use of tryptan blue or crystal violet is avoided. In a particular aspect of the invention, the photosensitiser used is other than tryptan blue and crystal violet, when a He Ne laser is used.

In a particular aspect of the invention the photosensitiser is targeted to the microbes and/or uptake of the photosensitiser by the microbes is enhanced by using a photosensitiser coupled to a targeting moiety. The targeting moiety may be any specific binding partner for a specific binding agent on the microbe, for instance an antibody against a surface antigen expressed by the microbe. Alternatively the targeting moiety may be a substance known to be actively taken up by the microbe. Coupling of the targeting moiety to the photosensitiser molecules may be achieved by use of conventional techniques. (see especially Friedberg, J. S. et al., *P.N.A.S., U.S.A.*, 618: 383–393 (1991)).

The laser light may be provided by any suitable source, such as a helium neon (HeNe) gas laser or a gallium arsenide (GaAs) laser, if necessary or convenient using fibre optics or other known optical devices to deliver the light to the site to be treated. HeNe gas laser light (at 632.8 nm) is particularly suitable as it has good penetration of oral tissues and blood and is absorbed well by the photosensitisers which are especially suitable for use in the present invention. However other photosensitiser/laser combinations may be contemplated and those skilled in the art will readily be able to adapt other known laser sources and photosensitisers for use in destroying disease-related microbes, particularly those known to infect wounds or to be present in the oral cavity.

Lasers which emit in the far red (700 to 800nm) may also be used, especially the semiconductor lasers. When such lasers are used, the photosensitisers selected will have an absorbtion peak at 700 nm or longer wavelength and may therefore be "colourless" but certain dyes, such as methylene blue may also be used with these lasers. Particularly preferred photosensitiser/laser combinations are:

(a) toluidine blue O with a helium/neon laser (wavelength 632.8 nm)
 (b) aluminium disulphonated phthalocyamine with a gallium aluminium arsenide laser (wavelength 660 nm).
 Combination (a) is especially applicable to the treatment of HIV-associated oral candidosis and periodontal diseases. Combination (b) is especially applicable to the treatment or prevention of caries. These form especially preferred aspects of the the present invention.

The amount of photosensitiser and laser dose required to destroy the microbes will vary with the microbe and the site to be treated. However it has been found that exposure of representative microbes commonly found in the oral cavity and implicated in inflammatory periodontal disease, caries and other dental diseases as set out below generally affords satisfactory destruction of the microbes:

1. Laser power: He Ne laser, 1 to 100 mw, preferably about 25 mW Ga As laser, 1 to 100 mW. preferably about 15 mW.
   Note: The laser source will be selected having regard to the choice of beam diameter, exposure time and sensitivity of the microbes to the laser/photosensitiser combination. Very powerful sources may be used for short durations or to irradiate a large area but it is generally preferred to use less powerful sources such that special precautions, other than eye protection which is always necessary, may be avoided.
2. Laser beam size: Beam diameters of from 1 to 10 mm are convenient for working in the oral cavity.

Duration of laser irradiation: 1 second to 5 minutes, preferably 5 seconds to 2 minutes and most preferably about 30 seconds.

Note: These figures apply to a single area, corresponding to the laser beam size, irradiated continuously or, if intermittently irradiated, to the total duration of irradiation of that area. When the area to be treated exceeds the beam size necessitating moving the beam, the total duration of the treatment will be correspondingly increased.
4. Light dose: 5 to 30 $J.cm^{-2}$, preferably 10 to 20 $J.cm^{-2}$ and most preferably about 15 $J.cm^{-2}$.

Sensitiser concentrations: 0.00001 to 1% w/v in aqueous solution, preferably 0.0001 to 0.1% w/v and more preferably 0.001 to 0.01% w/v, for instance 0.005% w/v It should be noted that the photosensitiser concentration is that at the site of treatment and, for instance in the treatment of periodontal pockets and wounds where the treatment site may be flooded with body fluid such as saliva or blood, it might be necessary to apply the photosensitiser in greater concentration so as to achieve an effective concentration after dilution by the body fluid.

The photosensitiser solution is left in contact with the microbes for a period of time to enable the microbes to take up some of the photosensitiser and become sensitive to the laser light. A suitable duration will generally be from 1 second to 10 minutes for instance 10 seconds to 2 minutes, preferably about 30 seconds although this may vary depending upon the particular photosensitiser in use and the target microbes to be destroyed.

Preferably the photosensitiser will be used in the form of a pharmaceutical composition comprising the photosensitiser in solution in a pharmaceutically acceptable aqueous carrier such as water, for instance distilled water or demineralised water, preferably pyrogen-free, sterile water or water for injection. The composition may additionally comprise buffers, salts for adjusting the tonicity of the solution, antioxidants, preservatives, gelling agents (such as guar and derivatives thereof and the like. Preferably the composition will be in the form of a physiologically buffered, isotonic aqueous solution comprising the photosensitiser at from 0.00001 to 10% w/v, preferably up to 1% w/v, for instance from 0.0001 to 0.1% w/v. In a particular aspect of the invention the composition is intended for treatment of enamel and/or dentine and/or gingival tissues and is formulated with remineralisation agents as well as photosensitising compound and accessory ingredients. Such compositions may be used in treatment of periodontal pockets, carious lesions and the like in order to improve the strength of the dental enamel and/or dentine simultaneously with destruction of disease-related microbes by laser irradiation. Remineralisation agents are well known in themselves and are used in conventional manner, for instance as described in Pearse, E. L. F. and Nelson, D. G. A., *Caries Research*, 22, 362–370 (1988).

It should be noted that the use of free radical and singlet oxygen scavenging materials should be avoided as these tend to interfere with the photosensitisation of microorganisms.

In accordance with the present invention, a photosensitiser solution at appropriate dilution will be applied topically to a site to be treated, such as a debrided wound or lesion, for instance a drilled-out carious lesion or periodontal pocket or a mucosal surface infected with *Candida albicans*, the photosensitiser solution will be left in contact with the microbes to be destroyed for a time sufficient for the microbes to take up an effective amount of the photosensitiser and the site will then be exposed to suitable laser irradiation at sufficient power and for sufficient duration to destroy at least a proportion and preferably all disease-related microbes at the site. Further treatment of the site, for instance filling the carious lesion or suturing the wound may then be undertaken.

The invention will now be illustrated by the following Examples which are not intended to limit the scope of invention in any way. The Examples show the use of photosensitisers and lasers to destroy a variety of organisms which are involved in oral diseases and are representative of the genera of microbes which infect wounds

EXAMPLE 1

Materials and Methods

Laser

The laser used was a Helium/Neon (HeNe) gas laser (NEC Corporation, Japan) with a power output of 7.3 mW. This emitted radiation in a collimated beam, diameter 1.3 mm, with a wavelength of 632.8 nm.

Target Organisms

The organisms used in the study were: *Streptococcus sanguis* NCTC 10904, *Porphyromonas gingivalis* W50, *Fusobacterium nucleatum* NCTC 10562 and *Actinobacillus actinomycetemcomitans* Y4. All were maintained by weekly transfer on Wilkins Chalgren (WC) blood agar (Oxoid Ltd., Basingstoke, UK) except for *S. sanguis* which was sub-cultured every 48 h on brain heart infusion (BHI) agar (Oxoid Ltd).

Photosensitisers

Test compounds were obtained from Sigma Ltd., Poole, UK, except as follows: Ariabel dark blue, FDC blue #2, ariavit patent blue, ariavit indigo carmine, arianor steel blue, ariavit brilliant blue FCF and usacert FD and C blue #1 and #2 (all from Williams Ltd., Hounslow, UK); azure mixture sicc. and azure B (Fluka, Buchs, Switzerland); brilliant cresyl blue and trypan blue (BDH, Poole, UK); aluminium disulphonated phthalocyanine (a gift from Prof. D. Phillips, Chemistry Dept., Imperial College, London); haematoporphyrin ester (Paisley Biochemicals Ltd., Glasgow).

Effect of Laser Light on Bacterial Viability

Several colonies of the test organism were suspended in sterile saline and vortexed to provide a homogeneous suspension. Portions of this suspension (2.0 ml) were mixed with portions of a solution (2.0 ml) of the test compound at various concentrations in saline (or saline alone in the case of controls) and a sample (1.0 ml) spread over the surfaces of agar plates. Excess fluid was removed (after 10 min.) and the plates dried at 37° C. The plates were then exposed to the laser for various periods of time, following which they were incubated in anaerobic jars until growth was visible on the control plates. The plates were examined for zones of inhibition and were then re-incubated for an additional 7 days to determine whether any growth occurred within the inhibition zones.

In the case of *S. sanguis* and *A. actinomycetemcomitans*, the medium used was BHI while for *P. gingivalis* and *F. nucleatum* this was supplemented with 0.0001% (w/v) menadione and 0.001% (w/v) haemin. Control plates in which the bacteria were not exposed to the test compound served to determine whether laser light alone had any effect on the viability of the target organisms. Any adverse effect on the Viability of the bacteria by the test compound itself was ascertained by examination of un-irradiated portions of those plates receiving bacteria previously exposed to the compound.

Screening of Compounds for Photosensitising Activity 27 compounds were tested for their ability to inhibit growth of *S. sanguis* following exposure to HeNe laser light. Each compound was tested at concentrations of 0.1% and 0.01% (wv) and exposure to the laser light was for 5, 10, 30 and 60s.

Effect of Varying the Concentration of Photosensitiser

Compounds shown to act as photosensitisers in the screening programme were selected for further investigation. Using the method described above, the effect of varying the concentration of the compound, and the light exposure time, on the growth of *S. sanguis* were determined. A range of concentrations from 0.00015% (w/v) to 0.01% (w/v) was used, each at an exposure time of 2, 10 and 30 s.

Photosensitisation of Other Oral Bacteria

Some of the most promising compounds were then tested for their ability to sensitise *P. gingivalis*,. *A. actinomycetemcomitans* and *F. nucleatum* to killing by HeNe light.

Results

The results of the initial screening programme of the 27 test compounds using *S. sanguis* as the target organism are shown in Table 1.

From this is can be seen that the following compounds were effective photosensitisers:arianor steel blue, toluidine blue O, crystal violet, methylene blue, thionin, several azure photosensitisers, haematoporphyrin and haematoporphyrin ester. Kill times ranged from 5 to 60 s which represented energy doses of 2.75 to 33 J/cm$^2$.

Zones of killing were not seen on control plates in which *S. sanguis* was irradiated without prior exposure of any of the test compounds. Except in the case of phthalocyanine, the test compounds themselves had no apparent effect on the growth of *S. sanguis* at the concentrations tested.

TABLE 1

| test compound | exposure time (s) | photosensitiser concentration (%, w/v) | result |
| --- | --- | --- | --- |
| brilliant blue FCF | 60 | 0.1 | − |
| ariavit patent blue V | 60 | 0.1 | − |
| usacert FD and C blue #1 | 60 | 0.1 | − |
| usacert FD and C blue #2 | 60 | 0.1 | − |
| arianor steel blue | 60 | 0.1 | + |
| ariabel turquoise | 60 | 0.1 | − |
| ariavit indigo carmine | 60 | 0.1 | − |
| patent blue VRS | 60 | 0.1 | − |
| toluidine blue O | 5 | 0.01 | + |
| crystal violet | 10 | 0.01 | + |
| methylene blue | 10 | 0.01 | + |
| azure blue cert | 5 | 0.01 | + |
| azure B chloride | 5 | 0.01 | + |
| azure 2 | 5 | 0.01 | + |
| azure A chloride | 5 | 0.01 | + |
| azure B tetrafluoroborate | 5 | 0.01 | + |
| thionin | 5 | 0.01 | + |
| azure A eosinate | 5 | 0.01 | + |
| azure B eosinate | 5 | 0.01 | + |
| azure mix sicc. | 5 | 0.01 | + |
| azure II eosinate | 5 | 0.01 | + |
| trypan blue | 60 | 0.1 | − |
| bromocresol blue | 60 | 0.01 | − |
| gallocyanin | 60 | 0.01 | − |
| haematoporphyrin HCl | 10 | 0.01 | + |
| haematoporphyrin ester | 5 | 0.01 | + |
| aluminium disulphonated phthalocyanine | DT | | |

+ = bactericidal effect
− = no detectable bactericidal effect
DT = direct toxicity shown to *S. sanguis*
The effect of light from a Helium/Neon laser on the survival of *S. sanctuis* following exposure to a range of test compounds is shown. In the case of a positive result (i.e. killing) the lowest concentration of photosensitiser tested is given in combination with the shortest exposure time used. For negative results (i.e. no killing) the highest photosensitiser concentration and longest exposure times are given.

The effect on *S. sanguis* of varying the concentrations of the most promising compounds selected from the preliminary screening programme was then investigated. Table 2 shows that, of the photosensitisers tested, toluidine blue O azure A chloride and thionin were the most effective at inducing killing of *S. sanguis*. In the case of toluidine blue O, for example, zones of killing were apparent in some experiments following irradiation for 2 s using a concentration of 0.0003% (w/v).

From Table 3 it can be seen that, of the photosensitisers tested, toluidine blue, methylene blue and azure B chloride were the only ones effective against all of the target organisms. In general, *F. nucleatum* and *A. actinomycetemcomitans* appeared to be more resistant to killing than *S. sanguis* and *P. gingivalis*, under the conditions of photosensitiser concentration and exposure time employed.

TABLE 2

| Photosensitiser | concentration (% w/v) | exposure time 2 s | 10 s | 30 s |
|---|---|---|---|---|
| toluidine blue O | 0.01 | + | + | + |
|  | 0.005 | + | + | + |
|  | 0.0025 | v | + | + |
|  | 0.00125 | v | + | + |
|  | 0.00063 | v | v | + |
|  | 0.00031 | v | v | v |
|  | 0.00016 | – | – | – |
| azure A chloride | 0.01 | v | + | + |
|  | 0.005 | v | + | + |
|  | 0.0025 | v | + | + |
|  | 0.00125 | v | v | + |
|  | 0.00063 | – | – | + |
|  | 0.00031 | – | – | – |
| crystal violet | 0.01 | + | + | + |
|  | 0.005 | v | v | + |
|  | 0.0025 | v | v | + |
|  | 0.00125 | – | – | + |
|  | 0.00063 | – | – | v |
|  | 0.00031 | – | – | – |
| thionin | 0.01 | + | + | + |
|  | 0.005 | + | + | + |
|  | 0.0025 | + | + | + |
|  | 0.00125 | + | + | + |

TABLE 2-continued

| Photosensitiser | concentration (% w/v) | exposure time 2 s | 10 s | 30 s |
|---|---|---|---|---|
|  | 0.00063 | v | + | + |
|  | 0.00031 | – | + | + |
|  | 0.00016 | – | v | + |
|  | 0.00008 | – | – | + |
| azure B chloride | 0.01 | – | + | + |
|  | 0.005 | – | + | + |
|  | 0.0025 | – | – | v |
|  | 0.00125 | – | – | – |
| azure B fluoroborate | 0.01 | – | v | + |
|  | 0.005 | – | – | + |
|  | 0.0025 | – | – | v |
|  | 0.00125 | – | – | – |
| methylene blue | 0.01 | + | + | + |
|  | 0.005 | – | + | + |
|  | 0.0025 | – | – | + |
|  | 0.00125 | – | – | – |
| haematoporphyrin ester | 0.01 | + | + | + |
|  | 0.005 | + | + | + |
|  | 0.0025 | – | + | + |
|  | 0.00125 | – | – | – |
| aluminium disulphonated phthalocyanine | 0.01 | NT | | |
|  | 0.005 | NT | | |
|  | 0.0025 | – | + | + |
|  | 0.00125 | – | + | + |
|  | 0.00063 | – | + | + |
|  | 0.00031 | – | – | + |
|  | 0.00016 | – | – | + |
| haematoporphyrin HCl | 0.01 | – | + | + |
|  | 0.005 | – | – | + |
|  | 0.0025 | – | – | – |

+ = bactericidal effect
– = no detectable bactericidal effect
v = variable results
NT = not tested because of direct toxicity of photosensitiser to *S. sanguis* at these concentrations
The effect of irradiation time on the survival of *S. sanguis* following treatment with various concentrations of photosensitising agents is shown.

TABLE 3

| photosensitiser | exposure time (s) | S. sanguis | A. actinomycetemcomitans | F. nucleatum | P. gingivalis |
|---|---|---|---|---|---|
| toluidine blue O (0.005%) | 10 | + | v | + | + |
|  | 30 | + | + | + | + |
| haematoporphyrin HCl (0.5 mM) | 10 | + | – | – | + |
|  | 30 | + | – | – | + |
| crystal violet (0.005%) | 10 | + | – | – | v |
|  | 30 | + | – | – | v |
| thionin (0.005%) | 10 | + | – | – | – |
|  | 30 | + | – | – | – |
| azure B chloride (0.005%) | 10 | + | v | + | + |
|  | 30 | + | v | + | + |
| methylene blue (0.005%) | 10 | + | + | + | + |
|  | 30 | + | + | + | + |
| aluminium disulphonated phthalocyanine (0.0025%) | 30 | + | – | – | + |
| haematoporphyrin ester (0.005%) | 10 | + | – | – | + |
|  | 30 | + | + | – | + |

+ = bactericidal effect
– = no detectable bactericidal effect
v = variable results
The susceptibility of various oral bacteria to light from a HeNe laser following exposure to a range of photosensitisers is shown.

Discussion

The results of this investigation Rave demonstrated that a number of compounds can sensitise several species of oral bacteria, both Gram-positive and Gram-negative, to killing by light from a HeNe laser. Irradiation of the bacteria in the absence of the photosensitisers had no detectable effect on the viability of these organisms and, at the concentrations tested, the photosensitisers themselves did not exert a bactericidal effect. Of the compounds exhibiting photosensitising activity, those with absorption maxima closest to the wavelength of the radiation emitted by the laser (632.8 nm) were among the most effective. These included toluidine blue (632.2 nm) and azure A chloride (632.4 nm).

The present investigation shows that haematoporphyrin HCl and haematoporphyrin ester were capable of sensitising both Gram-positive and Gram-negative bacteria to killing by HeNe light. Since these compounds absorb poorly at 632.8 nm, this finding was surprising.

One of the newer generation of tumour photosensitisers, aluminium disulphonated phthalocyanine, was also found to be an effective photosensitiser of Gram-positive and Gram-negative bacteria in the present investigation. In general, however, the photosensitisers developed for use in the photochemotherapy (PCT) of tumours were less effective at sensitising bacteria to killing by HeNe light than photosensitisers such as toluidine blue, thionin and some azure photosensitisers.

Of the 16 compounds found to be photosensitisers of *S. sanguis*, toluidine blue, methylene blue and azure B chloride also proved to be effective sensitisers of *P. gingivalis*, *F. nucleatum* and *A. actinomycetemcomitans*. At a concentration of 0.005% (w/v) these compounds enabled killing of the organisms following exposure to HeNe light for only 30 s. Since these organisms are involved in a number of oral infections, including gingivitis and periodontitis, these results imply that the invention is effective in treating such infections. Furthermore, the topical nature of such diseases renders them particularly amenable to this form of treatment since the lesions are readily accessible to the photosensitiser and to the light.

EXAMPLE 2

A gallium arsenide laser with a wavelength of 660 nm (power=15 mw) was used in conjunction with aluminium disulphonated phthalocyanine and tested against *Streptococcus mutans*, *S. sobrinus*, *Lactobacillus casei*, *L. fermentum* and *Actinomyces viscosus*, all of which are involved in dental caries.

The experimental methodology was similar to that used in Example 1 except that tryptone soya broth was used instead of saline. Results are shown in Table 4.

TABLE 4

| Organism | exposure time (s) | photosensitiser concentration (% w/v) | result |
|---|---|---|---|
| S. mutans | 15 | 0.01 | − |
|  | 30 | 0.01 | − |
|  | 60 | 0.01 | + |
|  | 60 | 0.001 | + |
| S. sobrinus | 30 | 0.01 | + |
|  | 120 | 0.001 | + |
| L. casei | 15 | 0.01 | + |
|  | 30 | 0.001 | + |
| L. fermentum | 30 | 0.01 | + |

TABLE 4-continued

| Organism | exposure time (s) | photosensitiser concentration (% w/v) | result |
|---|---|---|---|
|  | 120 | 0.001 | + |
| A. viscosus | 15 | 0.01 | + |
|  | 30 | 0.001 | + |

The energy densities required to kill these organisms are therefore up to 2.8 j/cm$^2$ (for a photosensitiser concentration of 0.001% and an exposure time of 120 s)

EXAMPLE 3

Lethal Photosensitisation of *Salmonella enteritidis*

An overnight culture of *Salmonella enteritidis* was prepared and diluted 1/10 and 1/100 in saline. An equal volume of 0.01% (w/v) toluidine blue O was added to each and 1.0 ml of each suspension was spread over the surface of nutrient agar plates. Excess fluid was removed and the plates dried at 37° C. The plates were then exposed to light from a HeNe laser for 30 s and 60 s. They were then incubated overnight and inspected for zones of inhibition.

Zones of inhibition were apparent after 60 s irradiation using the 1/10 dilution of the suspension.

EXAMPLE 4

Lethal Photosensitisation of *Candida albicans*

An overnight culture of *Candida albicans* in Sabouraud broth was prepared and equal volumes of various concentrations of toluidine blue O in saline were added to aliquots of the suspension. 1.0 ml of these suspensions were added to Sabouraud dextrose agar plates, excess fluid removed, the plates dried and then exposed to light from a 7.3 mW HeNe laser for various periods of time. Following incubation, zones of inhibition were apparent as shown in Table 5.

TABLE 5

| | exposure time (s) | | | | | | | |
|---|---|---|---|---|---|---|---|---|
| dye concen. (%) | 15 | 30 | 45 | 60 | 120 | 180 | 240 | 300 |
| 0.1 | + | + | + | + | + | + | + | + |
| 0.01 | − | − | − | + | + | + | + | + |
| 0.001 | − | − | − | − | − | − | − | − |
| 0.0001 | − | − | − | − | − | − | − | − |
| 0.00001 | − | − | − | − | − | − | − | − |

+ = zone of inhibition seen
− = no zone of inhibition seen

EXAMPLE 5

Lethal Photosensitisation of *Candida albicans*

Methods

A gallium aluminium arsenside (GaAs) diode laser (Omega Universal Technologies, London) with a power output of 11 mW (beam diameter=9 mm, wavelength=660 nm) was used in conjunction with the photosensitisers aluminium disulphonated phthalocyanine (ADP) and methylene blue (MB, C.I. 52015). A helium/neon (HeNe) gas laser (NEC Corporation, Japan) with a power output of 7.3 mW (beam diameter=1.3 mm, wavelength=632.8 nm) was used in conjunction with crystal violet (CV, C.I. 42555), toluidine blue O (TBO, C.I. 52040, dihaematoporphyrin ester (DHE) and thionin (C.I. 52000). 50 μl aliquots of an overnight culture of *C. albicans* diluted 1:100 with sterile brain heart infusion (BHI) broth were transferred to wells of a micro-titre plate and an equal volume of a solution of the photosensitiser in BHI was added to each well to give a final concentration of either 0.1, 0.5 or 1.0 mg/ml. After 5 min incubation at room temperature, duplicate wells (gently stirred) were exposed to light from the laser for 120 s. Control wells containing the yeast suspension plus BHI in place of the dye solution were treated in an identical manner. A further 4 wells, identical to those described above, were prepared and these were not exposed to laser light. After irradiation of appropriate wells the number of survivors was determined by viable counting.

On the basis of these experiments, the most promising photosensitisers were selected and their effectiveness in inducing killing of a more dense suspension of yeast cells was determined. The experimental protocol was as outlined above except that the overnight yeast culture was diluted 1:10 rather than 1:100 and each dye was used at a concentration of 0.1 mg/ml.

Results

The effects on the viability of *C. albicans* of exposure to TBO, laser light and a combination of both are shown in Table 6. Exposure to HeNe light for 120 s had no statistically significant effect on the viability of the yeast (Student's t-test, p>0.05). However, TBO at concentrations of 0.1 and 0.5 mg/ml, in the absence of HeNe laser light, reduced the viable count of suspensions of the organism by 20.1% and 23.9% respectively. There was a statistically significant reduction in the viable count when yeast suspensions were irradiated with HeNe light for 120 s in the presence of TBO (energy does=0.88 J at a density of 66.3 J/cm$^2$). The number of organisms killed increased with increasing dye concentration, amounting to 64.1% and 69.6% at concentrations of 0.1 and 0.5 mg/ml respectively.

In the absence of HeNe laser light, thionin had no statistically significant effect on yeast viability at concentrations of 0.1 and 0.5 mg/ml (Table 6). However, irradiation of the yeast with HeNe light for 120 s in the presence of thionin resulted in statistically significant reductions in viability.

Neither light from the Here laser nor CV at concentrations of 0.1 and 0.5 mg/ml had a statistically significant effect on the viability of the yeast. However, statistically significant reductions is viability were achieved when the yeast was irradiated with HeNe light in the presence of the dye.

DHE at a concentration as high as 2.5 mg/ml was unable to sensitise *C. albicans* to killing by HeNe laser light even when the exposure time was as long as 360 s.

When used alone, neither the HeNe light nor 0.1 mg/ml TBO had a significant effect on the viability of a more-concentrated yeast suspension (Table 6). However, exposure of the organism to HeNe laser light in the presence of 0.1 mg/ml TBO resulted in a significant reduction (p<0.0001) in viable count. At a concentration of 0.1 mg/ml, thionin was toxic to the yeast in the absence of laser light. When the more-concentrated yeast suspension was exposed to the HeNe light for 120 s in the presence of the dye, a much greater reduction in viable count was obtained.

0.1 mg/ml CV was toxic to the yeast in the absence of laser light, but a greater reduction in the viable count was achieved when the dye-treated suspension was irradiated with HeNe laser light for 120 s (Table 6).

Exposure to light from a GaAs laser for 120 s (energy dose=1.32 J at a density of 2.04 J/Cm$^2$) had no statistically significant effect on yeast viability in the absence of ADP. ADP was toxic to the yeast at a concentration of 1.0 mg/ml, causing a significant reduction (p=0.002) in the viable count of 43.5%. However, 0.1 mg/ml ADP had no significant effect on yeast viability. When the yeast suspensions were irradiated with light from the GaAs laser in the presence of 1.0 mg/ml ADP the resulting viable counts were significantly lower than those of the unirradiated, dye-free control. However, there was no significant difference between the counts of the irradiated and unirradiated dye-treated suspensions.

In the absence of GaAs laser light, MB was toxic to *C. albicans*. At concentrations of 0.1 and 1.0 mg/ml the viable counts of yeast suspensions were reduced by 16.9% and 35.2% respectively. When the yeast was exposed to light from the GaAs laser for 120 s in the presence of the due the viable counts were significantly lower than those resulting from treatment with the dye in the absence of laser light. The reductions amounted to 42.1% and 59.4% when the dye was used at concentrations of 0.1 and 1.0 mg/ml respectively. Light from the GaAs laser had no significant effect on the viability of the yeast when used in the absence of the dye.

These results demonstrate the *C. albicans* can be killed by short term exposure to light from the low-power lasers once the organism has been treated with an appropriate photo-sensitiser. In the case of the HeNe laser, TBO was the most effective sensitiser while MB was the most effective when the GaAs laser was used.

TABLE 6

| Photosensitiser | Photosensitiser concentration (mg/ml) | % reduction in viable count | | |
|---|---|---|---|---|
| | | D – L+ | D + L– | D + L+ |
| (a) using a 1/100 dilution of an overnight culture of *C. albicans* | | | | |
| TBO | 0.1 | NS | 20.1 | 64.1 |
| | 0.5 | NS | 23.9 | 69.6 |
| Thionin | 0.1 | NS | NS | 29.5 |
| | 0.5 | NS | NS | 39.9 |
| CV | 0.1 | NS | NS | 79.5 |
| | 0.5 | NS | NS | 90.6 |
| (b) using a 1/10 dilution of an overnight culture of *C. albicans* | | | | |
| TBO | 0.1 | NS | NS | 77.4 |
| Thionin | 0.1 | NS | 12.8 | 69.4 |
| CV | 0.1 | NS | 3.1 | 21.8 |

D – L+ = exposed to laser in the absence of dye;
D + L– = exposed to dye but not laser;
D + L+ = exposed to laser in the present of dye;
NS = not significantly different from control cultures exposed to neither laser nor dye.
Effect of light from a HeNe laser on the viability of suspensions of *C. albicans* is shown.

EXAMPLE 6

Model of in vitro Use

Lethal Photosensitisation of Subgingival Plaque Samples

Using an experimental protocol similar to that of Example 5, subgingival plaque samples from 20 patients with chronic periodontitis were exposed to light from a 7.3 mW HeNe laser for 30 s in the presence and absence of 50 μg/ml toluidine blue O as a photosensitiser. Viable counts of various groups and species of bacteria were carried out before and after irradiation using a variety of selective and non-selective media. The median numbers of viable bacteria initially present in the 30 μl aliquots irradiated were $1.13 \times 10^3$ cfu (aerobes), $4.08 \times 10^3$ cfu (anaerobes), $4.92 \times 10^3$ cfu (black-pigmented anaerobes), $4.75 \times 10^2$ cfu (*Porphyromonas gingivalis*), $6.15 \times 10^3$ cfu (*Fusobacterium nucleatum*) and $1.7 \times 10^3$ cfu (streptococci). The dye/laser combination achieved significant reductions in the viability of these organisms, the median percentage reductions in the viable counts being 91.1% for aerobes, 96.6% for anaerobes, 100% for black-pigmented anaerobes, *P. gingivalis* and *F. nucleatum* and 94.2% for streptococci. Overall, the viability of bacteria in the twenty plaque samples was not significantly decreased by the dye alone. This demonstrates that lethal photosensitisation of periodontopathogenic bacteria can be achieved when these organisms are present as constituents of the highly-mixed subgingival plaque microflora characteristic of patients with chronic periodontitis.

EXAMPLE 7

Model of in vivo Use

Lethal Photosensitisation of Cariogenic Bacteria when Shielded by Dentine or when Embedded in a Collagen Matrix The purpose of this investigation was to determine if killing was possible (i) following passage of the laser light through dentine slices and (ii) when the bacteria were embedded in a collagen matrix.

Methods (i) Dentine slices (200 μm thick) from a human molar were demineralised with 0.1 M EDTA for 8, 16, 24 and 32 h. Equal volumes of an overnight culture of *Streptococcus mutans* and 0.05% TBO were placed in a well of a microtitre plate. The suspension was exposed to light from a 7.3 mW HeNe laser for 240 s, with interposition of one of the dentine slices. Bacteria were enumerated before and after exposure. The experiment was repeated using ADP as a photosensitiser in conjunction with an 11 mW GaAs laser.

(ii) A suspension of *S. mutans* in a collagen gel was dried overnight to form a bacteria-containing plug. TBO (or ADP) was added and the plug exposed to the HeNe (or GaAs) laser for 60 s. The plug was digested with collagenase and surviving bacteria enumerated.

Results (i) When dentine slices were interposed between the HeNe laser and the bacterial suspensions, substantial kills were achieved. These ranged from $1.8 \times 10^6$ to $3.66 \times 10^7$ cfu. There was no relationship between the extent of killing and the time for which the dentine slices were demineralised. In the case of the ADP/GaAs combination, a similar pattern of results was obtained. The numbers killed ranged from $1.2 \times 10^6$ to $1.34 \times 10^7$ cfu. Again, there was no relationship between the extent of killing and the demineralisation time.

(ii). Following irradiation of the bacteria-containing collagen plugs, the numbers of bacteria killed were $8.94 \times 10^8$ and $2.08 \times 10^8$ cfu respectively for the TBO/HeNe and ADP/GaAs systems. Controls showed no statistically significant kill when either the dye or the laser were used alone.

The results of this investigation have shown that photosensitised-*S. mutans* can be killed by low-power laser light even when the light has passed throug 200 μm thick sections of human dentine and when the bacteria are embedded in a collagen matrix. This shows that lethal photosensitisation of this cariogenic organism can be achieved under conditions which resemble more closely the situation found in a caries lesion in vivo.

EXAMPLE 8

Model of in vivo Use

Lethal Photosensitisation of *Candida albicans* in the Presence of Serum

In an oral lesion caused by *C. albicans*, the cells will invariably be in a serum-rich environment. As serum may interfere with lethal photosensitisation (eg by complexing with the photosensitiser) it is important to deterine whether killing can be achieved in its presence. The following experiment, therefore, was undertaken.

$2 \times 5$ ml aliquots of an overnight culture of *C. albicans* were centrifuged, aliquots were resuspended, one in 50 ml of sterile BHI broth and the other in 50 ml of horse serum. The effect of HeNe laser light (120 s exposure) on the viability of the organism in the presence of 0.1 mg/ml of TBO was then determined as described in earlier Examples above.

In the absence of serum, the percentage kill in a suspension containing $3.74 \times 10^5$ cfu was 60% whle in the presence of serum the percentage kill was 66%. These results demonstrate that horse serum does not interfere with HeNe laser light-induced killing of TBO-sensitised *C. albicans*.

EXAMPLE 9

Use of a Gel Delivery System 0.5 g of guar hydroxypropyl derivative (BDH Ltd) was dissolved in 100 ml of water to form a gel and toluidine blue 0 added to 50 ml of the gel to give a final concentration of 100 μg/ml. Aliquots of the dye-containing and dye-free gel were added to suspensions of *Streptococcus mutans* and exposed to light from a HeNe laser for 240 s. Unirradiated bacteria-containing gels were used as controls. The numbers of surviving organisms in each gel were determined by viable counting.

There was a considerable reduction ($3.35 \times 10^7$ cfu) in the viable count of the organism in the gel containing toluidine blue demonstrating that lethal photosensitisation of *S. mutans* can be achieved when the photosensitiser is present in a gel carrier.

We claim:

1. A method of disinfecting or sterilising a locus wherein said locus is selected from the group consisting of tissues of the oral cavity and wounds and lesions in the oral cavity, said method comprising topically applying a photosensitising compound to said locus and irradiating said locus with laser light at a wave length absorbed by said photosensitising compound, so as to destroy microbes at said locus.

2. A method according to claim 1 wherein the method is selected from the group consisting of:

(a) destroying disease-related microbes in a periodontal pocket in order to treat chronic periodontitis;

(b) destroying disease-related microbes in the region between the tooth and gingiva in order to treat inflammatory periodontal diseases;

(c) destroying disease-related microbes in the region between the tooth and gingiva in order to prevent inflammatory periodontal diseases;

(d) disinfecting drilled-out carious lesions prior to filling;

(e) sterilising drilled-out carious lesions prior to filling;

(f) destroying cariogenic microbes on a tooth surface in order to treat dental caries;

(g) destroying cariogenic microbes on a tooth surface in order to prevent dental carries;

(h) disinfecting dental tissues in dental surgical procedures;

(i) disinfecting gingival tissues in dental surgical procedures;

(j) sterilising dental tissues in dental surgical procedures;

(k) sterilising gingival tissues in dental surgical procedures;

(l) treating oral candidiasis in AIDS patients;

(m) treating oral candidiasis in immunocompromised patients; and (n) treating oral candidiasis in patients with denture stomatitis.

3. A method according to claim 2 wherein said photosensitiser is selected from the group consisting of arianor steel blue, toluidine blue O, crystal violet, methylene blue, azure blue cert, azure B chloride, azure 2, azure A chloride, azure B tetrafluoroborate, thionin, azure A eosinate, azure B eosinate, azure mix sicc., azure II eosinate, haematoporphyrin HCl, haematoporphyrin ester, aluminium disulphonated phthalocyanine and chlorins.

4. A method according to claim 3 wherein said laser light is from a laser selected from the group consisting of helium neon gas lasers and gallium arsenide lasers.

5. A method according to claim 4 wherein said laser has a power of from 1 to 100 mW and a beam diameter of from 1 to 10 mm.

6. A method according to claim 4 wherein said laser irradiation is conducted for a duration of from one second to five minutes and a light dose of from 5 to 30 J·cm$^{-2}$ is administered.

7. A method according to claim 5 wherein said laser irradiation is conducted for a duration of from one second to five minutes and a light dose of from 5 to 30 J·cm$^{-2}$ is administered.

8. A method according to claim 3 wherein said photosensitiser is present at said locus at a concentration of 0.00001 to 1% w/v.

9. A method according to claim 3 wherein said photosensitiser is used in the form of a pharmaceutical composition comprising said photosensitiser in solution in a pharmaceutically acceptable aqueous carrier.

10. A method according to claim 9 wherein said pharmaceutical composition further comprises a least one accessory ingredient selected from the group consisting of buffers, salts for adjusting the tonicity of said solution, antioxidants, preservatives, gelling agents and remineralisation agents.

11. A method according to claim 10 wherein said laser light is from a laser selected from the group consisting of helium neon gas lasers and gallium arsenide lasers.

12. A method according to claim 11 wherein said laser has a power of from 1 to 100 mW and a beam diameter of from 1 to 10 mm.

13. A method according to claim 11 wherein said laser irradiation is conducted for a duration of from one second to five minutes and a light dose of from 5 to 30 J·cm$^{-2}$ is administered.

14. A method according to claim 12 wherein said laser irradiation is conducted for a duration of from one second to five minutes and a light dose of from 5 to 30 J·cm$^{-2}$ is administered.

15. A method according to claim 2 wherein said laser light is from a laser selected from the group consisting of helium neon gas lasers and gallium arsenide lasers.

16. A method according to claim 15 wherein said laser has a power of from 1 to 100 mW and a beam diameter of from 1 to 10 mm.

17. A method according to claim 15 wherein said laser irradiation is conducted for a duration of from one second to five minutes and a light dose of from 5 to 30 J·cm$^{-2}$ is administered.

18. A method according to claim 16 wherein said laser irradiation is conducted for a duration of from one second to five minutes and a light dose of from 5 to 30 J·cm$^{-2}$ is administered.

* * * * *